US006831076B2

(12) United States Patent
Hoefle et al.

(10) Patent No.: US 6,831,076 B2
(45) Date of Patent: Dec. 14, 2004

(54) EPOTHILONS C AND D, PREPARATION AND COMPOSITIONS

(75) Inventors: Gerhard Hoefle, Braunschweig (DE); Michael Kiffe, Braunschweig (DE)

(73) Assignee: Gesellschaft fur Biotechnologische Forschung mbH (GBF), Braunschweig (DE)

( * ) Notice: Subject to any disclaimer, the term of this patent is extended or adjusted under 35 U.S.C. 154(b) by 0 days.

(21) Appl. No.: 10/602,770

(22) Filed: Jun. 25, 2003

(65) Prior Publication Data

US 2004/0087634 A1 May 6, 2004

Related U.S. Application Data

(62) Division of application No. 09/836,134, filed on Apr. 16, 2001, now Pat. No. 6,613,912, which is a division of application No. 09/077,055, filed as application No. PCT/EP96/05080 on Nov. 18, 1996, now Pat. No. 6,288,237.

(30) Foreign Application Priority Data

Nov. 17, 1995 (DE) .......................... 195 42 986
Sep. 25, 1996 (DE) .......................... 196 39 456

(51) Int. Cl.$^7$ ................... A61K 31/335; A61K 31/425; C07D 417/06
(52) U.S. Cl. ................... 514/183; 514/365; 548/202; 548/204; 556/437; 549/214
(58) Field of Search .............................. 548/203, 204; 548/202; 514/365, 183; 556/437; 549/214

(56) References Cited

U.S. PATENT DOCUMENTS

| 6,194,181 B1 | 2/2001 | Hofmann et al. |
| 6,204,388 B1 | 3/2001 | Danishefsky et al. |

FOREIGN PATENT DOCUMENTS

| DE | 4138042.8 | 5/1993 |
| DE | 19542986.9 | 5/1997 |
| DE | 19639456.2 | 5/1997 |
| DE | 19636343.8 | 3/1998 |
| DE | 19645361.5 | 4/1998 |
| DE | 19645362.3 | 4/1998 |
| DE | 19647580.5 | 5/1998 |
| DE | 19701758 | 7/1998 |
| DE | 19707505.3 | 9/1998 |
| DE | 19713970 | 10/1998 |
| DE | 19720312 | 11/1998 |
| DE | 19821954 | 11/1998 |
| DE | 19726627 | 12/1998 |
| EP | 879 605 | 11/1998 |
| WO | 93/10121 | 5/1993 |
| WO | 97/19086 | 5/1997 |
| WO | 98/08849 | 3/1998 |
| WO | 98/22461 | 5/1998 |
| WO | 98/24427 | 6/1998 |
| WO | 98/25929 | 6/1998 |
| WO | 98/38192 | 9/1998 |
| WO | 98/47891 | 10/1998 |
| WO | 99/01124 | 1/1999 |
| WO | 99/03848 | 1/1999 |
| WO | 99/07692 | 2/1999 |
| WO | 99/39694 | 8/1999 |
| WO | 99/42602 | 8/1999 |
| WO | 99/43320 | 9/1999 |
| WO | 99/43653 | 9/1999 |
| WO | 00/00485 | 1/2000 |
| WO | 00/37473 | 6/2000 |
| WO | 00/66589 | 11/2000 |

OTHER PUBLICATIONS

Balog, A., et al., "Total Synthesis of (–)–Epothilone A", *Angew, Chem. Int. Ed. Engl.*, vol. 35, No. 23/24, 2801–2803 (1996).

Bertini, F., et al., "Alkenes from Epoxides by Reductive Elimination with Magnesium Bromide–Magnesium Amalgam", *Chem. Commun.*, 144 (1970).

Bollag, D.M., et al., "Epothilones, A New Class of Microtubule–stabilizing Agents with a Taxol–like Mechanism of Action", *Cancer Res.* 55, No. 11, 2325–2333 (1995).

Fujisawa, T., et al., "Deoxygenation of Epoxides to Olefins with $FeCl_3$–n–BuLi System", *Chem. Lett.*, 883–886 (1974).

Fujiwara, Y., et al., "Reductive Coupling of Carbonyl Compounds to Olefins by Tungsten Hexachloride–Lithium Aluminum Hydride and Some Tungsten and Molybdenum Carbonyls", *J. Org. Chem.*, vol. 43, No. 12, 2477–2479 (1978).

Gladysz, J. A., et al., "Deoxygenation of Epoxides by Metal Atom Cocondensation", *J. Org. Chem.*, vol. 41, No. 22, 3647–3648 (1976).

Hofle, G., et al., "Epothilone A and B—Novel 16–Membered Macrolides with Cytotoxic Activity: Isolation, Crystal Structure, and Conformation in Solution", *Angew. Chem. Int. Ed. Engl.*, vol. 35, No. 13/14, 1567–1569 (1996).

Hofle, G., et al., "N–Oxidation of Epothilone A–C and O–Acyl Rearrangement to C–19 and C–21 –Substituted Epothilones", *Angew. Chem. Int. Ed.*, vol. 38, No. 13/14, 1971–1974 (1999).

Inokuchi, T., et al., "Opening of Epoxides to Olefins or Halohydrins with Vanadium(II)–Tetrahydrofuran or Vanadium(III)–Tetrahydrofuran Complexes", *Synlett*, No. 6, 510–512 (1992).

Kowalski, R. J., et al., "Activities of the Microtubule–stabilizing Agents Epothilones A and B with Purified Tubulin and in Cells Resistant to Paclitaxel (Taxol®)" *J. Biol. Chem.*, vol. 272, No. 4, 2534–2541 (1997).

Kupchan, S. M., et al., "Reductive Elimination of Epoxides to Olefins with Zinc–Copper Couple", *J. Org. Chem.*, vol. 36, No. 9, 1187–1190 (1971).

Martin, M. G., et al., "Epoxides as Alkene Protecting Groups. A Mild and Efficient Deoxygenation", *Tetrahedron Letters*, vol. 25, No. 3, 251–254 (1984).

(List continued on next page.)

*Primary Examiner*—Golam M M Shameem
(74) *Attorney, Agent, or Firm*—Mathews, Collins, Shepherd & McKay, P.A.

(57) ABSTRACT

The present invention relates to epothilon derivatives and to their use.

6 Claims, No Drawings

OTHER PUBLICATIONS

McMurry, J. E., et al., "Reduction of Epoxides to Olefins with Low Valent Titanium", *J. Org. Chem.,* vol. 40, No. 17, 2555–2556 (1975).

McMurry, J. E., et al., "Some Deoxygenation Reactions with Low–Valent Titanium (TiCl$_3$/LiAlH$_4$)", *J. Org. Chem.,* vol. 43, No. 17, 3249–3254 (1978).

Meng, D., et al., "Remote Effects in Macrolide Formation Through Ring–Forming Olefin Metathesis: An Application to the Synthesis of Fully Active Epothilone Congeners", *J. Am. Chem. Soc.,* vol. 119, No. 11, 2733–2734 (1997).

Nicolaou, K. C., et al., "An Approach to Epothilones Based on Olefin Metathesis", *Angew. Chem. Int. Ed. Engl.,* vol. 35, No. 20, 2399–2401 (1996).

Nicolaou, K. C., et al., "Total Synthesis of Epothilone A: The Macrolactonization Approach", *Angew. Chem. Int. Ed. Engl.,* vol. 36, No. 5, 525–527 (1997).

Nicolaou, K. C., et al., "Designed Epothilones: Combinatorial Synthesis, Tubulin Assembly Properties, and Cytotoxic Action against Taxol–Resistant Tumor Cells",*Angew. Chem. Int. Ed. Engl.,* vol. 36, No. 19, 2097–2103 (1997).

Nicolaou, K.C., et al., "The Olefin Metathesis Approach to Epothilone A and Its Analogues", *J. Am. Chem. Soc.,* vol. 119, No. 34, 7960–7973 (1997).

Nicolaou, K. C., et al., "Total Syntheses of Epothilones A and B via a Macrolactonization–Based Strategy", *J. Am. Chem. Soc.,* vol. 119, No. 34, 7974–7991 (1997).

Nicolaou, K. C., et al., "Synthesis of Epothilones A and B in Solid and Solution Phase", *Nature,* vol. 387, 268–272 (1997).

Nicolaou, K. C., et al., "Synthesis of Epothilones A and B in Solid and Solution Phase" (Correction to *Nature* 387, 268–272 (1997), *Nature,* 390, 100 (1997).

Raucher, S., et al., "Total Synthesis of (+)–Dihydrocostunolide via Tandem Cope–Claisen Rearrangement", *J. Org. Chem.,* vol. 51, No. 26, 5503–5505 (1986).

Sato, M, et al., "Reduction of Organic Compounds with Low–Valent Niobium (NbCl$_5$/NaAlH$_4$)", *Chem. Letters,* 157–160 (1982).

Schinzer, D., et al., "Total Synthesis of (–)–Epothilone A", *Angew. Chem. Int. Ed. Engl.,* vol. 36, No. 5, 523–524 (1997).

Schobert, R., et al., "Reduction and Isomerization of Oxiranes and α–Diazoketones by Various Early Transition Metallocenes", *Synlett,* vol. 8, 465–466 (1990).

Sharpless, K. B., et al., "Lower Valent Tungsten Halides. A New Class of Reagents for Deoxygenation of Organic Molecules", *J. Amer. Chem. Soc.,* vol. 94, No. 18, 6538–6540 (1972).

Su, D.–S., et al., "Total Synthesis of (–)–Epothilone B: An Extension of the Suzuki Coupling Method and Insights into Structure–Activity Relationships of the Epothilones",*Angew. Chem. Int Ed. Engl.,* vol. 36, No. 7, 757–759 (1997).

Su, D.–S., et al., "Structure–Activity Relationships of the Epothilones and the First In Vivo Comparison with Paclitaxel", *Angew. Chem. Int. Ed. Engl.,* vol. 36, No. 19, 2093–2096 (1997).

Victory, S. F., et al., "Relative Stereochemistry and Solution Conformation of the Novel Paclitaxel–Like Antimitotic Agent Epothilone A", *Bioorg. Med. Chem. Letts.,* vol. 6., No. 7, 893–898 (1996).

Winkler, J. D., et al., "A Model For The Taxol (Paclitaxel)/Epothilone Pharmacophore",*Boorg. Med. Chem. Letts.,* vol. 6, No. 24, 2963–2966 (1996).

Yang, Z., et al., "Total Synthesis of Epothilone A: The Olefin Metathesis Approach",*Angew. Chem. Int. Ed. Engl.,* vol. 36, No. 1/2, 166–168 (1997).

Bollag, D., et al., "Epothilone, A New Structural Class of Microtubule Stabilizer", Abstract, *Proc. Am. Assoc. Cancer Res.,* vol. 36, 86 Meet. 454 (1995).

Bollag, D., "Epothilones: Novel Microtubule–Stabilising Agents",*Expert Opin. Invest. Drugs,* vol. 6, No. 7, 867–873 (1997).

Bertinato, P., et al., "Studies Toward a Synthesis of Epothilone A: Stereocontrolled Assembly of the Acyl Region and Models for Macrocylization", J. Org. Chem., vol. 61, No. 23, 8000–8001 (1996).

*Chemical & Engineering News,* "Epothilone Epiphany: Total Syntheses", vol. 74, No. 52, 24–26 (1996).

*Chemical & Engineering News,* "First Total Synthesis of Epothilone B", vol. 75, No. 13, 23 (1997).

*Chemical & Engineering News,* "Solid–Phase Epothilone Synthesis Used to Create Analog Library", vol. 75, No. 20, 33 (1997).

Claus, E., et al., "Synthesis of the C1–C9 Segment of Epothilons", *Tetrahedron Lett.,* vol. 38, No. 8, 1359–1362 (1997).

De Brabander, J., et al., "Towards a Synthesis of Epothilone A: Rapid Assembly of the C1–C6 and C7–C12 Fragments", *Synlett,* vol. 7, 824–826 (1997).

Gabriel, T. and Wessjohann, L., "The Chromium–Reformatsky Reaction: Asymmetric Synthesis of the Aldol Fragment of the Cytotoxic Epothilons from 3–(2–Bromoacyl)–2–Oxazolidinones", *Tetrahedron Lett.,* vol. 38, No. 8, 1363–1366 (1997).

Gerth, K., et al., "Epothilons A and B: Antifungal and Cytotoxic Compunds from *Sorangiusm cellulosum* (Myxobacteria) Production, Physico–chemical and Biological Properties", *J. Antibiotics,* vol. 49, No. 6, 560–563 (1996).

Marshall, A., "Total Synthesis of Epothilone", *Nature Biotechnology,* vol. 15, No. 3, 205 (1997).

Meng, D., et al., "Studies Toward a Synthesis of Epothilone A: Use of Hydropyran Templates for the Managment of Acyclic Stereochemical Relationships",*J. Org. Chem.,* vol. 61, No. 23, 7998–7999 (1996).

Meng, D., et al., "Total Syntheses of Epothilones A and B", *J. Am. Chem. Soc.,* vol. 119, No. 42, 10073–10092 (1997).

Mensching, S. and Kalesse, M., "Generation of Thiazoles by Column Dehydrogenation of Thiazolidines with MnO$_2$",*J. Prakt. Chem.,* vol. 339, No. 1, 96–97 (1997).

Mulzer, J. and Mantoulidis, A., "Synthesis of the C(1)–C–(9) Segment of the Cytotoxic Macrolides Epothilon A and B", *Tetrahedron Lett.,* vol. 37, No. 51, 9179–9182 (1996).

Nicolaou, K, et al., "Chemistry, Biology and Medicine of Selected Tubulin Polymerizing Agents", *Pure Appl. Chem.,* vol. 71, No. 6, 989–997 (1999).

Nicolaou, K., et al., "Total Synthesis of Epothilone E and Related Side–chain Modified Analogues Via a Stille Coupling Based Strategy", *Bioorg. Med. Chem.,* vol. 7, No. 5, 665–697 (1999).

Schinzer, D., et al., "Studies Towards the Total Synthesis of Epothilones: Asymmetric Synthesis of the Key Fragments", *Chem. Eur. J.,* vol. 2, No. 22, 1477–1482 (1996).

Taylor, R. and Haley, J., "Towards the Synthesis of Epothilone A: Enantioselective Preparation of the Thiazole Sidechain and Macrocyclic Ring Closure", *Tetrahedron Lett.,* vol. 38, No. 12, 2061–2064 (1997).

Schinzer, D., et al., "Syntheses of (–)–Epothilone A", *Chem. Eur. J.,* vol. 5, No. 9, 2483–2491 (1999).

Schinzer, D., et al., "Syntheses of (–)–Epothilone B", *Chem. Eur. J.,* vol. 5, No. 9, 2492–2500 (1999).

Nicolaou, K. C., "Synthesis and Biological Properties of C12,13–Cyclopropylepothilone A and Related Epothilones", *Chemistry & Biology,* vol. 5, No. 7, 365–372 (1998).

Altmann, K.H., et al., "Epothilones and Related Structures—A New Class of Microtubule Inhibitors With Patent In Vivo Antitumor Activity," Biochim. Biophys Acta, 1470 (2000).

EPOTHILONS C AND D, PREPARATION AND COMPOSITIONS

CROSS REFERENCE TO RELATED APPLICATION

This a divisional of Ser. No. 09/836,134, filed Apr. 16, 2001, now U.S. Pat. No. 6,613,912 B2 issued Sep. 2, 2003, which in turn is a divisional of Ser. No. 09/077,055, filed Aug. 3, 1998, now U.S. Pat. No. 6,288,237 B1 issued Sep. 11, 2001, the latter corresponding under 35 U.S.C. §371 to PCT/EP96/05080, filed Nov. 18, 1996.

The present invention relates generally to epothilon derivatives and to their use in the preparation of medicaments. The present invention relates especially to the preparation of epothilon derivatives of general formulae 1 to 7 shown hereinafter and to their use in the preparation of therapeutic compositions and compositions for plant protection.

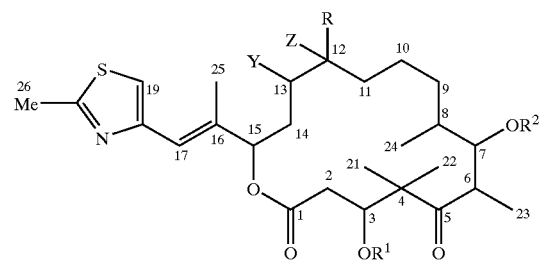

1

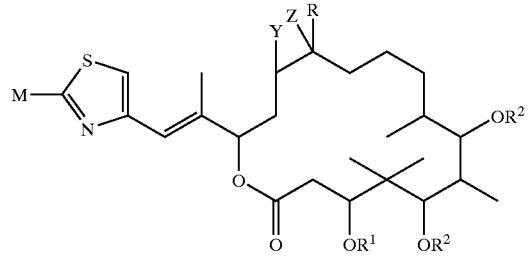

2

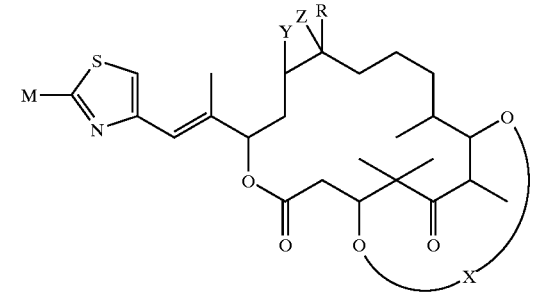

3

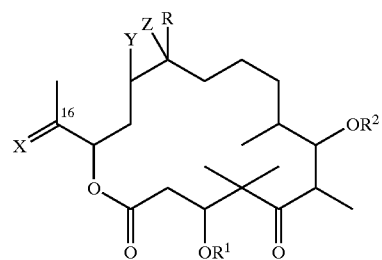

4

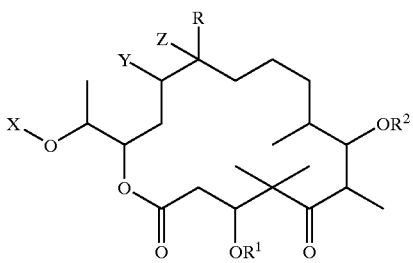

5

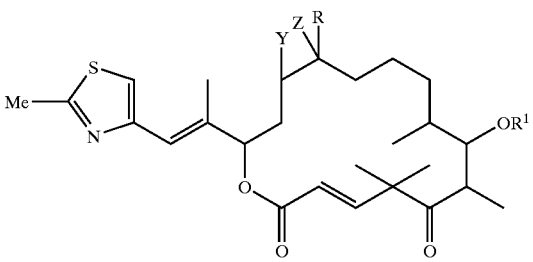

6

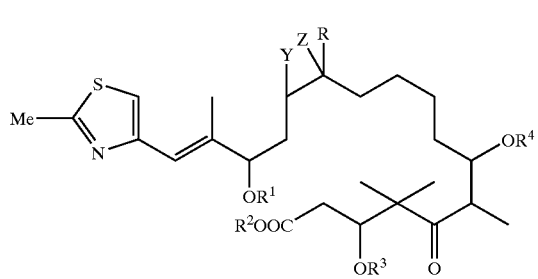

7

In formulae 1 to 7 given above:

R=H, $C_{1-4}$alkyl;

$R^1$, $R^2$, $R^3$, $R^4$, $R^5$=H, $C_{1-6}$alkyl,
$C_{1-6}$acyl-benzoyl,
$C_{1-4}$trialkylsilyl,
benzyl,
phenyl,
benzyl or phenyl each substituted by $C_{1-6}$alkoxy, $C_6$alkyl, hydroxy or by halogen;

it also being possible for two of the radicals $R^1$ to $R^5$ to occur together to form a group —$(CH_2)_n$— wherein n is from 1 to 6, and the alkyl and acyl groups contained in the radicals are straight-chain or branched radicals;

Y and Z are either identical or different and each represents hydrogen, halogen, such as F, Cl, Br or I, pseudohalogen, such as —NCO, —NCS or —$N_3$, OH, O—($C_{1-5}$)acyl, O—($C_{1-6}$)alkyl, O-benzoyl. Y and Z may also be the O atom of an epoxy group, epothilon A and B not being claimed, or one of the C—C bonds forms a C=C double bond.

In formula 3, X generally represents —C(O)—, —C(S)—, —S(O)—, —$CR^1R^2$—, wherein $R^1$ and $R^2$ are as defined above, or —$SiR_2$— wherein R is as defined above.

In formula 4, X represents oxygen, $NOR^3$, N—$NR^4R^5$ or N—$NHCONR^4R^5$, wherein the radicals $R^3$ to $R^5$ are as defined above.

In formula 5, X represents hydrogen, $C_{1-18}$alkyl, $C_{1-18}$acyl, benzyl, benzoyl or cinnamoyl.

For epothilons A and B, see DE-A-41 38 042.

Compounds according to general formula 1 can be obtained starting from epothilon A and B and from their 3-O— and/or 7-O-protected derivatives by opening the 12,13-epoxy group. If hydrohalic acids are used for that purpose in a preferably non-aqueous solvent, there being obtained the halohydrins X=Hal, Y=OH and Y=OH, Y=Hal. Protonic acids, such as, for xample, toluenesulphonic acid and trifluoroacetic acid, result, in the presence of water, in 12,13-diols which are then acylated (e.g. with carboxylic acid anhydrides and pyridine or triethylamine/DMAP) or alkylated (alkylhalides and silver oxide) according to standard processes. For that purpose, the 3- and 7-hydroxy groups may be protected temporarily in the form of a formate (removal with $NH_3$/MeOH) or of a p-methoxybenzyl ether (removal with DDQ).

Compounds according to general formula 2 are obtainable from epothilon A and B and also from their 3-O- and/or 7-O-protected derivatives by reduction, for example with $NaBH_4$ in methanol. If 3-OH and/or 7-OH are protected reversibly, then after acylation or alkylation and removal of the protecting groups there may be obtained 5-O-monosubstituted or 3,5- or 5,7-O-disubstituted derivatives of general formula 2.

Reactions of epothilon A and B with bifunctional electrophilic reagents, such as (thio)phosgene, (thio)carbonyldiimidazole, thionyl chloride or dialkylsilyl dichlorides or bistriflates yield compounds of general formula 3. Pyridine, trialkylamines, optionally together with DMAP or 2,6-lutidine in an aprotic solvent serve as auxiliary bases in the process. The 3,7-acetals of general formula 3 are produced by transacetalisation, for example of dimethylacetals in the presence of an acid catalyst.

Compounds according to general formula 4 are obtained from epothilon A and B or from 3-O- and/or 7-O—protected derivatives thereof by ozonolysis and reductive treatment, for example with dimethyl sulphide. The C-16-ketones may then be converted Into oximes, hydrazones or semicarbazones in accordance with standard processes known to the person skilled in the art. They are, moreover, converted into C-16-/C-17-olefins by Wittig, Wittig-Horner, Julia or Petersen olefination.

The 16-hydroxy derivatives according to general formula 5 are obtainable by reduction of the C-16-keto group, for example with an aluminium hydride or borohydride. If 3-OH and 7-OH are provided with suitable protecting groups, the 16-hydroxy derivatives may be either acylated or alkylated. The 3-OH and 7-OH groups are freed, for example, in the case of O-formyl by $NH_3$/MeOH and, in the case of O-p-methoxybenzyl, by DDQ.

The compounds of general formula 6 are obtained from derivatives of epothilon A and B, in which the 7-OH group has been protected by acyl or ether groups, by, for example, formylating, mesylating or tosylating the 3-OH group and then eliminating it by treatment with a base, for example DBU. The 7-OH group can be freed as described above.

Compounds of general formula 7 are obtained from epothilon A and B or from 3-OH- and 7-OH-protected derivatives thereof by basic hydrolysis, for example with NaOH in MeOH or MeOH/water. Preferably compounds of general formula 7 are obtained from epothilon A or B or from 3-OH— or 7-OH-protected derivatives thereof by enzymatic hydrolysis, especially with esterases or lipases. The carboxy group can be converted to an ester with a diazoalkane after protection of the 19-OH group by alkylation.

Moreover, compounds of formula 7 may be converted into compounds of formula 1 by lactonisation in accordance with the methods of Yamaguchi (trichlorobenzoyl chloride/DMAP), Corey (aldrithiol/triphenylphosphine) or Kellogg (omega-bromic acid/caesium carbonate). Relevant working methods may be found in Inanaga et al. in Bull. Chem. Soc. Japan, 52 (1979) 1989; Corey & Nicolaou in J. Am. Chem. Soc., 96 (1974) 5614; and Kruizinga & Kellogg in J. Am. Chem. Soc., 103 (1981) 5183.

To prepare the compounds according to the invention, it is also possible to start from epothilon C or D, where, for the derivatisation, reference may be made to the derivatisation methods described above. The 12,13-double bond may be selectively hydrogenated, for example catalytically or with diimine; or epoxidised, for example with dimethyldioxirane or with a peracid; or converted Into a dihalide, dipseudohalide or diazide.

The invention relates also to compositions for plant protection in agriculture, forestry and/or horticulture, consisting of one or more of the above-mentioned epothilon derivatives or consisting of one or more of the above-mentioned epothilon derivatives together with one or more common carrier(s) and/or diluent(s).

Finally, the invention relates to therapeutic compositions consisting of one or more of the above-mentioned compounds or of one or more of the above-mentioned compounds together with one or more common carrier(s) and/or diluent(s). These compositions may especially demonstrate cytotoxic activities and/or cause immunosuppression and/or be used to combat malignant tumours; they are particularity preferred as cytostatic agents.

The invention is illustrated and described hereinafter in greater detail by the description of a number of selected embodiments.

EXAMPLES

Example 1

Compound 1a 20 mg (0.041 mmol) of epothilon A are dissolved in 1 ml of acetone, 50 µl (0.649 mmol) of trifluoroacetic acid are added and the reaction mixture is stirred overnight at 50° C. The reaction mixture is worked up by adding 1M phosphate buffer pH 7 and extracting the aqueous phase four times with ethyl acetate. The combined organic phases are washed with saturated sodium chloride solution, dried over sodium sulphate and freed of solvent. The raw product is purified by preparative layer chromatography (eluant:dichloromethane/acetone, 85:15).

Yield:

4 mg (19%) of isomer I 4 mg (19%) of isomer II

Isomer I $R_1$ (dichloromethane/acetone, 85:15): 0.46

IR (film): $ny$ = 3440 (m, b, sh), 2946 (s, sh), 1734 (vs), 1686 (m), 1456 (m), 1375 (w), 1256 (s, sh), 1190 (w, b, sh), 1071 (m, sh), 884 (w), 735 (w) cm$^{-1}$.

MS (20/70 eV): m/e (%) = 493 (43 [M—$H_2O$]$^+$), 394 (47), 306 (32), 206 (30), 181 (40), 166 (72), 139 (100), 113 (19), 71 (19), 57 (24), 43 (24).

Microanalysis: $C_{26}H_{39}O_6NS$ calc.: 493.2498 for [M–$H_2O$]$^+$ found: 493.2478

Isomer II $R_1$(dichloromethane/acetone, 85:15): 0.22

IR (film): ny = 3484 (s, b, sh), 2942 (vs, sh), 1727 (vs), 1570 (w), 1456 (m), 1380 (m), 1265 (s), 1190 (w), 1069 (m), 975 (w) cm$^{-1}$.

MS (20/70 eV): m/e (%) = 493 (21 [M—H$_2$O]$^+$), 394 (12), 306 (46), 206 (37), 181 (63), 166 (99), 139 (100), 113 (21), 71 (23), 57 (33), 43 (28).

Microanalysis: $C_{26}H_{39}O_6NS$ calc.: 493.2498 for [M–H$_2$O]$^+$ found: 493.2475

Example 2

Compound 1b 55 mg (0.111 mmol) of epothilon A are dissolved in 0.5 ml of tetrahydrofuran, 0.5 ml of 1N hydrochloric acid is added, and the reaction mixture is stirred at room temperature for 30 minutes. 1N Phosphate buffer pH 7 is then added and the aqueous phase is extracted four times with ethyl acetate. The combined organic phases are washed with saturated sodium chloride solution, dried over sodium sulphate and freed of solvent. The raw product is purified by preparative layer chromatography (eluant: dichloromethane/methanol, 90:10). Yield: 19 mg (32%).

$R_1$ (dichloromethane/methanol, 90:10): 0.46

IR film): ny=3441 (s, br, sh), 2948 (s, sh), 1725 (vs, sh), 1462 (m), 1381 (w), 1265 (m), 1154 (w), 972 (m, br, sh) cm$^{-1}$.

UV (methanol): lambda$_{max}$ (lg epsilon)=210 (4.29), 248 (4.11) nm.

MS (20/70 eV): m/e (%) 529 (13 [M$^+$]), 494 (10), 342 (38), 306 (23), 194 (32), 164 (100), 140 (31), 113 (15), 57 (16).

Microanalysis: $C_{26}H_{40}O_6ClNS$ calc.: 529.2265 for [M$^{30}$], found: 529.2280

Example 3

Compound 1c 25 mg (0.047 mmol) of 12-chloro-13-hydroxy-epothilon A (1b) are dissolved in 1 ml of dichloromethane, and 29 mg (0.235 mmol) of dimethylaminopyridine, 151 µl (1.081 mmol) of triethylamine and 20 µl (0.517 mmol) of 98% formic acid are added. The reaction mixture is cooled with ice/salt. When –15° C. has been reached, 40 µl (0.423 mmol) of acetic anhydride are added to the reaction mixture, which is stirred for 70 minutes at –15° C. Since thin-layer chromatography shows that the reaction is not complete, a further 6 mg (0.047 mmol) of dimethylaminopyridine, 7 µl (0.047 mmol) of triethylamine, 2 µl of 98% formic acid (0.047 mmol) and 4 µl (0.047 mmol) of acetic anhydride are added to the reaction mixture, which is stirred for 60 minutes. The reaction mixture is worked up by heating to room temperature, adding 1M phosphate buffer pH 7 and extracting the aqueous phase four times with ethyl acetate. The combined organic phases are washed with saturated sodium chloride solution, dried over sodium sulphate and freed of solvent. The raw product is purified by preparative layer chromatography (eluant: dichloromethane/acetone, 90:10).

Yield: 5 mg (1 8%).

$R_1$ (dichloromethane/acetone, 90:10): 0.67

IR (film): ny = 3497 (w, b, sh), 2940 (s, b, sh), 1725 (vs), 1468

(m, b, sh), 1379 (m), 1265 (s), 1253 (s), 1175 (vs), 972

(m, b, sh), 737 (s) cm$^{-1}$.

MS (20/70 eV): m/e (%) = 613 (9 [M$^+$]), 567 (43), 472 (63), 382 (23), 352 (21), 164 (100), 151 (33), 96 (31), 69 (17), 44 (26).

Microanalysis: $C_{29}H_{40}O_9NSCl$ calc.: 613.2112 for [M$^+$]

found: 613.2131

Example 4

Compound 1d 10 mg (0.020 mmol) of epothilon B are dissolved in 0.5 ml of tetrahydrofuran, 0.5 ml of 1N hydrochloric acid is added and the reaction mixture is stirred at room temperature for 30 minutes. 1M Phosphate buffer pH 7 is then added and the aqueous phase is extracted four times with ethyl acetate. The combined organic phases are washed with saturated sodium chloride solution, dried over sodium sulphate and freed of solvent. The raw product is purified by preparative layer chromatography (eluant:dichloromethane/acetone, 85:15).

Yield: 1 mg (9%).

$R_1$ (dichloromethane/acetone, 85:15): 0.38

MS (20/70 eV): m/e (%) = 543 (3 [M$^+$]), 507 (14), 320 (19), 234 (9), 194 (17), 182 (23), 164 (100), 140 (22), 113 (14), 71 (13).

Microanalysis: $C_{27}H_{42}O_6NSCl$ calc.: 543.2421 for [M$^+$]

found: 543.2405

Example 5

Compound 2a 100 mg (0.203 mmol) of epothilon A are dissolved in 4 ml of tetrahydrofuran/-1M phosphate buffer pH 7 (1:1), and sodium borohydride (150 mg=3.965 mmol) is added until the starting material has reacted completely according to thin-layer chromatography. Dilution with 1M phosphate buffer pH 7 is then carried out and the aqueous phase is extracted four times with ethyl acetate. The combined organic phases are washed with saturated sodium chloride solution, dried over sodium sulphate and freed of solvent. The raw product is purified by silica chromatography (eluant:dichloromethane/acetone, 95:5—gradient—to dichloromethane/acetone, 85:15).

Yield: (20%)

$R_1$ (dichloromethane/acetone, 75:25): 0.27

IR (film): ny = 3413 (s, b, sh), 2965 (vs, sh), 1734 (vs), 1458 (m, b, sh), 1383 (m, sh), 1264 (s, b, sh), 1184 (m, b, sh), 1059

(s, sh), 966 (s), 885 (w), 737 (m) cm$^{-1}$.

-continued

MS (20/70 eV): m/e (%) = 495 (6 [M$^+$]), 477 (8), 452 (12), 394 (9), 364 (16), 306 (49), 194 (19), 178 (35), 164 (100), 140 (40), 83 (21), 55 (27).

Microanalysis: $C_{26}H_{41}O_6NS$ calc.: 495.2655 for [M$^+$]
found: 495.2623

Example 6

Compound 3a–d (a–d are Stereoisomers)

100 mg (0.203 mmol) of epothilon A are dissolved in 3 ml of pyridine, 50 µl (0.686 mmol) of thionyl chloride are added and the reaction mixture is stirred at room temperature for 15 minutes. 1M Phosphate buffer pH 7 is then added and the aqueous phase is extracted four times with ethyl acetate. The combined organic phases are washed with saturated sodium chloride solution, dried over sodium sulphate and freed of solvent. The crude product is purified and the four stereoisomers 3a–d are separated by preparative layer chromatography (eluant: toluene/methanol, 90:10).

Compound 3a
  Yield: 4 mg (12%)
  $R_1$ (toluene/methanol, 90:10): 0.50

IR (film): ny = 2961 (m, b, sh), 1742 (vs), 1701 (vs), 1465 (m, sh), 1389 (m, sh), 1238 (s, sh), 1210 (vs, sh), 1011 (s, sh), 957 (s, b, sh), 808 (m, sh), 768 (s, sh) cm$^{-1}$.

UV (methanol): lambda$_{max}$ (lg epsilon) = 210 (4.50), 248 (4.35) nm.

MS (20/70 eV): m/e (%) = 539 (40[M$^+$]), 457 (22), 362 (16), 316 (27), 222 (30), 178 (30), 164 (100), 151 (43), 96 (38), 69 (29), 55 (28), 43 (20).

Microanalysis: $C_{26}H_{37}O_7NS_2$ calc.: 539.2011 for [M$^+$]

Compound 3b
  Yield: 14 mg (13%)
  $R_1$ (toluene/methanol, 90:10): 0.44

IR (film) ny = 2963 (s, br, sh), 1740 (vs), 1703 (s), 1510 (w), 1464

(m, br, sh), 1389 (m, sh), 1240 (s, br, sh), 1142 (m), 1076

(w), 1037 (w), 1003 (m), 945 (s, br, sh), 806 (m, sh), 775 (s), 737 (m) cm$^{-1}$.

UV (methanol): lambda$_{max}$(lg epsilon)=211 (4.16), 250 (4.08) nm.

MS (20/70 eV): m/e (%) = 539 (27 [M$^+$]), 475 (17), 322 (41), 306 (67), 222 (16), 206 (17), 194 (19), 178 (32), 164 (100), 151 (33), 125 (18), 113 (15), 96 (39), 81 (23), 64 (58), 57 (42), 41 (19).

Microanalysis: $C_{26}H_{37}O_7NS_2$ calc.: 539.2011 for [M$^+$]
found: 539.1998

Compound 3c
  Yield: 4 mg (4%)
  $R_1$ (toluene/methanol, 90:10): 0.38

MS (20/70 eV): m/e (%) = 539 (69 [M$^+$]), 322 (22), 306 (53), 222 (36), 178 (31), 164 (100), 151 (41), 96 (25), 81 (20), 69 (26), 55 (25), 41 (25)

Microanalysis: $C_{26}H_{37}O_7NS_2$ calc.: 539.2011 for [M$^+$]
found: 539.2001

Compound 3d
  Yield: 1 mg (1%)
  $R_1$ (toluene/methanol, 90:10): 0.33

MS(20/70 eV): m/e(%) = 539(69[M$^+$]), 322(35), 306(51),

222(41), 178(31), 164(100), 151(46),

96(31), 81(26), 69(34), 55(33), 41(35)

Microanalysis: $C_{26}H_{37}O_7NS_2$ calc.: 539.2011 for [M$^+$]
found: 539.1997

Example 7

Compound 4a 10 mg (0.020 mmol) of epothilon A are dissolved in 2 ml of dichloromethane, cooled to −70° C. and then treated with ozone for 5 minutes until there is a slight blue coloration. 0.5 ml of dimethyl sulphide is subsequently added to the resulting reaction mixture, which is heated to room temperature. The reaction mixture is worked up by freeing it of solvent and finally by preparative layer chromatography (eluant:dichloromethane/-acetone/methanol, 85:10:5).

Yield: 5 mg (64%)
  $R_1$ (dichloromethane/acetone/methanol, 85:10:5): 0.61

IR (film): ny = 3468 (s, br, sh), 2947 (s, br, sh), 1734 (vs, sh), 1458 (w), 1380 (w), 1267 (w), 1157 (w), 1080 (w), 982 (w) cm$^{-1}$.

UV (methanol): lambda$_{max}$ (lg epsilon)=202 (3.53) nm.

MS (20/70 eV): m/e (%) = 398 (2 [M$^+$]), 380 (4), 267 (14), 249 (17), 211 (20), 193 (26), 171 (34), 139 (34), 111 (40), 96 (100), 71 (48), 43 (50).

Microanalysis: $C_{21}H_{34}O_7$: calc.: 398.2305 for [M$^+$]
found: 398.2295

Example 8

Compound 6a 10 mg (0.018 mmol) of 3,7-di-O-formyl-epothilon A are dissolved in 1 ml of dichloromethane, 27 µl (0.180 mmol) of 1,8-diazabicyclo[5.4.0]undec-7-ene (DBU) are added and the reaction mixture is stirred at room temperature for 60 minutes. The reaction mixture is worked up by adding 1M sodium dihydrogen phosphate buffer pH 4.5 and extracting the aqueous phase four times with ethyl acetate. The combined organic phases are washed with saturated sodium chloride solution, dried over sodium sulphate and freed of solvent. After the solvent has been removed, the resulting raw product is dissolved in 1 ml of methanol, 200 µl of an ammoniacal methanol solution (2 mmol NH$_3$/ml methanol)

are added and the mixture is stirred overnight at room temperature. For separation, the solvent is removed in vacuo.

Yield: 4 mg (22%)

$R_1$ (dichloromethane/acetone, 85:15): 0.46

IR (film): ny = 3445 (w, br, sh), 2950 (vs, br, sh), 1717 (vs, sh), 1644 (w), 1466 (m, sh), 1370 (m, sh), 1267 (s, br, sh), 1179 (s, sh), 984 (s, sh), 860 (w), 733 (m) cm$^{-1}$.

UV (methanol): lambda$_{max}$ (lg epsilon)=210 (4.16) nm.

MS (20/70 eV): m/e (%) = 475 (28 [M$^+$]), 380 (21), 322 (37), 318 (40), 304 (66), 178 (31), 166 (100), 151 (29), 140 (19), 96 (38), 81 (20), 57 (26).

Microanalysis: $C_{26}H_{37}O_5NS$ calc.: 475.2392 for [M$^+$] found: 475.2384

Example 9

Compound 6b 50 mg (0.091 mmol) of 3,7-di-O-formyl-epothilon A are dissolved in 1 ml of dichloroethane, 2 ml (0.013 mmol) of 1,8-diazabicyclo[5.4.0]undec-7-ene (DBU) are added and the reaction mixture is stirred for 12 hours at 90° C.

The reaction mixture is worked up by adding 1M sodium dihydrogen phosphate buffer pH 4.5 and extracting the aqueous phase four times with ethyl acetate. The combined organic phases are washed with saturated sodium chloride solution, dried over sodium sulphate and freed of solvent. The raw product, consisting of two compounds, Is purified by preparative layer chromatography (eluant:dichloromethane/acetone, 90:10).

Yield: 7 mg (15%)

Substance Code $R_1$ (dichloromethane/acetone, 90:10): 0.62

IR (film): ny = 2951 (m, br, sh), 1723 (vs), 1644 (w, br, sh), 1468 (w), 1377 (w), 1271 (m, br, sh), 1179 (s), 987 (m, br, sh), 735 (w, br, sh) cm$^{-1}$.

UV (methanol): lambda$_{max}$ (lg epsilon)=210 (4.44) nm.

MS (20/70 eV): m/e (%) = 503 (68 [M$^+$]), 408 (58), 390 (32), 334 (25), 316 (34), 220 (21), 206 (27), 194 (20), 181 (33), 164 (100), 151 (34), 139 (28), 113 (20), 96 (82), 81 (33), 67 (24), 55 (26), 43 (22).

Microanalysis: $C_{27}H_{37}O_6NS$ calc.: 503.2342 for [M$^+$] found: 503.2303

Example 10

Compound 6c 5 mg (0.009 mmol) of 3,7-di-O-acetyl-epothilon A are dissolved in 1 ml of methanol, 150 µl of an ammoniacal methanol solution (2 mmol NH$_3$/ml methanol) are added and the reaction mixture is stirred overnight at 50° C. For separation, the solvent is removed in vacuo. The raw product is purified by preparative layer chromatography (eluant: toluene/methanol, 90:10).

Yield: 3 mg (67%)

$R_1$ (dichloromethane/acetone, 90:10): 0.55

IR (film): ny = 2934 (s, b, sh), 1719 (vs, b, sh), 1641 (m), 1460 (m, sh), 1372 (s, sh), 1237 (vs, b, sh), 1179 (s, sh), 1020 (s), 963 (s, sh), 737 (vs) cm$^{-1}$.

UV (methanol): lambda$_{max}$ (lg epsilon)=210 (4.33) nm.

MS (20/70 eV): m/e (%) = 517 (57 [M$^+$]), 422 (58), 318 (31), 194 (20), 181 (34), 166 (100), 151 (31), 96 (96), 81 (32), 69 (27), 55 (29), 43 (69).

Microanalysis: $C_{28}H_{39}O_6NS$ calc.: 517.2498 for [M$^+$] found: 517.2492

Example 11

Compound 7a 20 mg (0.041 mmol) of epothilon A are dissolved in 0.5 ml of methanol, 0.5 ml of 1 N sodium hydroxide solution is added and the reaction mixture is stirred at room temperature for 5 minutes.

The reaction mixture is worked up by adding 1M phosphate buffer pH 7 and extracting the aqueous phase four times with ethyl acetate. The combined organic phases are washed with saturated sodium chloride solution, dried over sodium sulphate and freed of solvent. The raw product is purified by preparative layer chromatography (eluant: dichloromethane/methanol, 85:15).

Yield :11 mg (52%)

$R_1$ (dichloromethane/methanol, 85:15): 0.92

IR (film): ny = 3438 (s, br, sh), 2971 (vs, br, sh), 1703 (vs), 1507 (m), 1460 (s, sh), 1383 (m, sh), 1254 (w), 1190 (w, br, sh), 1011 (w, br, sh), 866 (w, br), 729 (s) cm$^{-1}$.

MS (20/70 eV): m/e (%)=423 (0.1 [M$^+$]), 323 (4), 168 (89), 140 (100), 85 (31), 57 (67).

Microanalysis: $C_{23}H_{37}O_4NS$ calc.: 423.2443 for [M$^+$] found: 423.2410

Example 12

Compound 7b 5 mg (0.009 mmol) of 7-O-acetyl-epothilon A are dissolved in 1 ml of methanol, 200 µl of an ammoniacal methanol solution (2 mmol NH$_3$/ml methanol) are added and the reaction mixture is stirred at 50° C. for two days. For separation, the solvent is removed in vacuo. The raw product is purified by preparative layer chromatography (eluant: toluene/methanol, 90:10).

Yield: 3 mg (59%)

$R_1$ (dichloromethane/methanol, 90:10): 0.63

IR (film): ny = 3441 (m, b, sh), 2946 (s, sh), 1732 (vs), 1600 (w), 1451 (m), 1375 (m), 1246 (s, b, sh), 1013 (m, b, sh) cm$^{-1}$.

UV (methanol): lambda$_{max}$ (lg epsilon)=211 (3.75), 247 (3.59) nm.

MS(20/70 eV): m/e (%) =

567(1[M$^+$]), 465(4), 422(7), 388(5), 194(5), 182(7), 168(65), 164(17), 140(100), 97(10), 71(22), 43(27).

Microanalysis: $C_{29}H_{45}O_8NS$ calc.: 567.2866 for [M$^+$] found: 567.2849

Example 13

50 mg of epothilon A are dissolved in 20 µl of dimethyl sulphoxide and diluted with 30 ml of phosphate buffer (pH 7.1, 30 mM). After the addition of 5 mg of pig liver esterase (Boehringer Mannheim), the mixture is stirred for 2 days at 30° C. The mixture is acidified to pH 5 with 2N HCl and the epothilonic acid 7 is extracted with ethyl acetate. The organic phase is dried with sodium sulphate and concentrated to dryness by evaporation in vacuo. Yield 48 mg (96%).

Example 14

48 mg of epothilonic A acid 7 are dissolved in 6 ml of abs. THF and, with stirring, 40 p1 µf triethylamine and 16 µl of 2,4,6-trichlorobenzoyl chloride are added. After 15 minutes, the precipitate is removed by filtration and the filtrate is added dropwise, within a period of 15 minutes, with rapid stirring, to a boiling solution of 20 mg of 4-dimethylaminopyridine in 200 ml of abs. toluene. After a further 10 minutes, the mixture is concentrated by evaporation in vacua and the residue is partitioned between ethyl acetate/citrate buffer (pH 4). After separation by preparative HPLC, the evaporation residue of the organic phase yields 15 mg of epothilon A.

Example 15

Epothilons C and D as Starting Materials

A. Production Strain and Culture Conditions Corresponding to the Epothilon Basic Patent.

B. Production using DSM 6773

75 litres of culture are grown as described in the basis patent and are used for inoculation in a production fermenter containing 700 litres of production medium consisting of 0.8% starch, 0.2% glucose, 0.2% soya flour, 0.2% yeast extract, 0.1% $CaCl_2 \times 2H_2O$, 0.1#$MgSO_4 \times 7H_2O$, 8 mg/litre of Fe-EDTA, pH=7.4 and optionally 15 litres of Amberlite XAD-16 adsorber resin. Fermentation takes 7 to 10 days at 30° C., with aeration with 2 m$^3$ air/h. The $pO_2$ is maintained at 30% by regulating the rotary speed.

C. Isolation

The adsorber resin is separated from the culture using a 0.7 m$_2$ 100-mesh process filter and is freed of polar impurities by washing with 3 bed volumes of water/methanol 2:1. Elution with 4 bed volumes of methanol yields a raw extract which is concentrated by evaporation in vacuo until the aqueous phase occurs. That is then extracted three times with the same volume of ethyl acetate. Concentration of the organic phase by evaporation yields 240 g of raw extract which is partitioned between methanol and heptane in order to separate lipophilic impurities. From the methanolic phase there are obtained by evaporation in vacuo 180 g of isolate which is fractionated in three portions over Sephadex LH-20 (20×100 cm column, 20 ml/min methanol). The epothilons are contained in the fraction which is eluted in the retention time from 240 to 300 minutes and which comprises a total of 72 g. To separate the epothilons, chromatography is carried out in three portions on Lichrosorb RP-18 (15 µm, 10×40 cm column, eluant 180 ml/min methanol/water 65:35). After epothilon A and B there are eluted epothilon C at $R_1$=90–95 min and epothilon D at $R_1$=100–110 min, which are obtained, after evaporation in vacuo, in each case in a yield of 0.3 g of a colourless oil.

D. Physical Properties

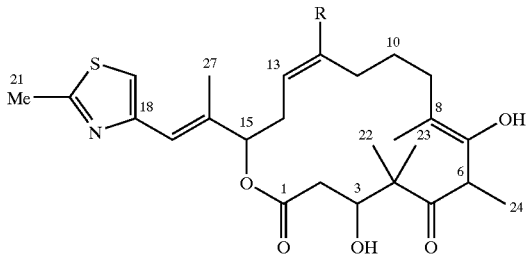

Epothilon C R═H

Epothilon D R═CH$_3$

Epothilon C $C_{26}H_{39}NO_6S$ [477]

ESI-MS : (positive ions): 478.5 for [M+H]$^+$ 1H and 13C, see NMR table

TLC: $R_1$=0.82

TLC aluminium foil 60 F 254 Merck, eluant:dichloromethane/methanol=9:1

Detection: UV extinction at 254 nm. Spraying with vanillin/sulphuric acid reagent, blue-grey coloration on heating to 1 20° C.

HPLC: $R_1$=11.5 min

Column: Nucleosil 100 C-18 7 µm, 125×4 mm.

Eluant: methanol/water=65:35

Flow rate: 1 ml/min

Detection: diode array

Epothilon D $C_{27}H_{41}NO_5S$[491]

ESI-MS: (positive ions): 492.5 for [M+H]$^+$ 1H and 13C, see NMR table

TLC: $R_1$=0.82

TLC aluminium foil 60 F 254 Merck, eluant:dichloromethane/methanol=9:1

Detection: UV extinction at 254 nm. Spraying with vanillin/sulphuric acid reagent, blue-grey coloration on heating to 120° C.

HPLC: $R_1$=15.3 min

Column: Nucleosil 100 C-18 7 µm, 125×4 mm

Eluant: methanol/water=65:35

Flow rate: 1 ml/min

Detection: diode array

TABLE $^1$H and $^{13}$C NMR data of epothilon C and epothilon D in [D$_6$]DMSO at 300 MHz

| H atom | Epothilon C δ (ppm) | C atom | δ (ppm) | Epothilon D δ (ppm) | C atom | δ (ppm) |
|---|---|---|---|---|---|---|
| | | 1 | 170.3 | | 1 | 170.1 |
| 2-Ha | 2.38 | 2 | 38.4 | 2.35 | 2 | 39.0 |
| 2-Hb | 2.50 | 3 | 71.2 | 2.38 | 3 | 70.8 |
| 3-H | 3.97 | 4 | 53.1 | 4.10 | 4 | 53.2 |
| 3-OH | 5.12 | 5 | 217.1 | 5.08 | 5 | 217.4 |
| 6-H | 3.07 | 6 | 45.4 | 3.11 | 6 | 44.4 |
| 7-H | 3.49 | 7 | 75.9 | 3.48 | 7 | 75.5 |
| 7-OH | 4.46 | 8 | 35.4 | 4.46 | 8 | 36.3 |
| 8-H | 1.34 | 9 | 27.6 | 1.29 | 9 | 29.9 |
| 9-Ha | 1.15 | 10 | 30.0 | 1.14 | 10 | 25.9 |
| 9-Hb | 1.40 | 11 | 27.6 | 1.38 | 11 | 31.8* |
| 10-Ha | 1.15* | 12 | 124.6 | 1.14* | 12 | 138.3 |
| 10-Hb | 1.35* | 13 | 133.1 | 1.35* | 13 | 120.3 |
| 11-Ha | 1.90 | 14 | 31.1 | 1.75 | 14 | 31.6* |
| 11-Hb | 2.18 | 15 | 76.3 | 2.10 | 15 | 76.6 |
| 12-H | 5.38** | 16 | 137.3 | | 16 | 137.2 |
| 13-H | 5.44** | 17 | 119.1 | 5.08 | 17 | 119.2 |
| 14-Ha | 2.35 | 18 | 152.1 | 2.30 | 18 | 152.1 |
| 14-Hb | 2.70 | 19 | 117.7 | 2.65 | 19 | 117.7 |
| 15-H | 5.27 | 20 | 164.2 | 5.29 | 20 | 164.3 |
| 17-H | 6.50 | 21 | 16.8 | 6.51 | 21 | 18.9 |
| 19-H | 7.35 | 22 | 20.8 | 7.35 | 22 | 19.7 |
| 21-H$_3$ | 2.65 | 23 | 22.6 | 2.65 | 23 | 22.5 |
| 22-H$_3$ | 0.94 | 24 | 16.7 | 0.90 | 24 | 16.4 |
| 23-H$_3$ | 1.21 | 25 | 18.4 | 1.19 | 25 | 18.4 |
| 24-H$_3$ | 1.06 | 27 | 14.2 | 1.07 | 26 | 22.9 |
| 25-H$_3$ | 0.90 | | | 0.91 | 27 | 14.1 |
| 26-H$_3$ | | | | 1.63 | | |
| 27-H$_3$ | 2.10 | | | 2.11 | | |

*, **allocation interchangeable

Example 16

Epothilon A and 12,13-bisepi-epothilon A from Epothilon C 50 mg of epothilon C are dissolved in 1.5 ml of acetone, and 1.5 ml of a 0.07M solution of dimethyldioxirane in acetone are added. After 6 hours' standing at room temperature, concentration by evaporation in vacuo is carried out and separation is effected by preparative HPLC on silica gel (eluant: methyl tert-butyl ether/petroleum ether/methanol 33:66:1).

Yield:

25 mg of epothilon A, R$_1$=3.5 min (analyt. HPLC, 7 μm, 4×250 mm column, eluant see above, flow rate 1.5 ml/min) and 20 mg of 12,13-bisepi-epothilon A, R$_1$=3.7 min, ESI-MS (pos. ions)

m/z=494 [M+H]$^+$ $^1$H-NMR in [D$_4$] methanol, selected signals:

delta=4.32 (3-H), 3.79 (7-H), 3.06 (12-H),
3.16 (13-H), 5.54 (15-H), 6.69 (17-H), 1.20 (22-H), 1.45 (23-H).

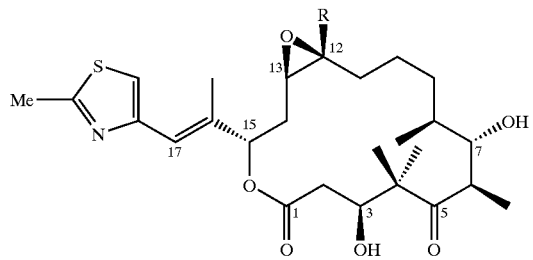

12,13-bisepi-epothilon A R=H

Example 17

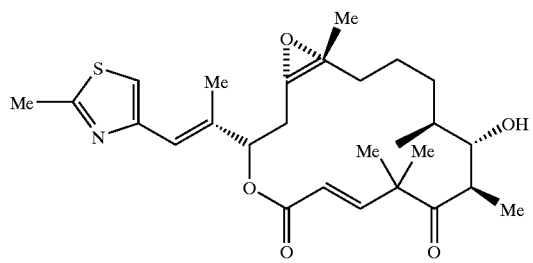

[1S-[1R*,3R*(E),10S*,11S*,12R*,16S*]]-11-Hydroxy-8,8,10,12,16-pentamethyl-3-[1-methyl-2-(2-methyl-4-thiazolyl)ethenyl]-4,17-dioxabicyclo[14.1.0]heptadec-6-ene-5,9-dione A. [1S-[1R*,3R*(E),7R*,10S*,11S*,12R*,16S*]]-7,11-Hydroxy-8,8,10,12,16-pentamethyl-3-[1-methyl-2-(2-methyl-4-thiazolyl)ethenyl]-4,17-dioxabicyclo[14.1.0]heptadecane-5,9-dione, 7,11-diformate.

Formic acid (0.95 ml, 25 mmol, 5.0 equiv), 4-N,N-dimethylaminopyridine (1.3 g, 11 mmol), and triethylamine (7.0 ml, 49 mmol) were added to a solution of epothilone B (2.5 g, 5.0 mmol) in CH$_2$Cl$_2$ (100 ml). The reaction mixture was cooled to −15° C. and acetic anhydride (2.3 ml, 25 mmol) was added over 5 minutes. The reaction mixture was stirred for 15 minutes at −15° C. then warmed to room temperature and stirred for 30 minutes. The reaction mixture was quenched with pH 7.0 phosphate buffer, and the organic layer extracted with CH$_2$Cl$_2$ (3×100 ml). The combined organic extracts were washed with 1 N HCl (1×100 ml) and 10% NaHCO$_3$ (1×100 ml). The organic layer was dried (Na$_2$SO$_4$), filtered, and concentrated under vacuum to give Compound A (2.8 g, 100%), a glassy solid, which was used without further purification.

MS (M+H)$^+$564

TLC: Rf=0.71 (9/1 CH$_2$Cl$_2$/acetone, visualization with UV)

B. [1S-[1R*,3R*(E),10S*,11S*,12R*,16S*]]-11-Formyloxy-8,8,10,12,16-pentamethyl-3-[1-methyl-2-(2-methyl-4-thiazolyl)ethenyl]-4,17-dioxabicyclo[14.1.0]heptadec-6-ene-5,9-dione, 11-formate.

1,8-Diazabicyclo[5.4.0]undec-7-ene (7.3 ml, 49 mmol, 10 equiv), was added over 5 minutes to a solution of Compound A (2.8 g, 4.9 mmol) in CH$_2$Cl$_2$ (140 ml) at room temperature. The reaction mixture was stirred at room temperature for one hour. The reaction mixture was quenched with pH 4.0 phosphate buffer and extracted with CH$_2$Cl$_2$ (3×200 ml).

The combined organic extracts were washed with 10% NaHCO$_3$ (1×200 ml). The organic layer was dried (Na$_2$SO$_4$), filtered, and concentrated under vacuum to afford Compound B (2.5 g, 100%), a glassy solid, which was used without further purification.

MS (M+H)$^+$518

TLC: Rf=0.76 (9/1 CH$_2$Cl$_2$/acetone, visualization with UV)

C. [1S-[1R*,3R*(E),10S*,11S*,12R*,16S*]]-11-Hydroxy-8,8,10,12,16-pentamethyl-3-[1-methyl-2-(2-methyl-4-thiazolyl)ethenyl]-4,17-dioxabicyclo[14.1.0]heptadec-6-ene-5,9-dione.

2M Ammonia in methanol (20 ml, 40 mmol) was added to a solution of Compound B (2,5 g, 4.8 mmol) in methanol (100 ml) at room temperature. The reaction mixture was stirred at room temperature for four hours. The reaction mixture was concentrated under vacuum. The residue was purified by flash chromatography (eluting with 19/1 CH$_2$Cl$_2$/acetone) to afford the title compound (2.1 g, 89%), as a glassy white solid.

MS (M+H)$^+$490

TLC: Rf=0.41 (9/1 CH$_2$Cl$_2$/acetone, visualization with UV)

Elemental analysis for C$_{27}$H$_{39}$NO$_8$S.0.22H$_2$O Calc: C, 65.70; H, 8.05; N, 2.84 Found: C, 65.69; H, 8.12; N, 2.77.

What is claimed is:

1. A compound of the formula:

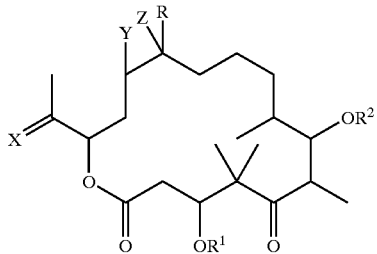

wherein

R is hydrogen or C$_{1-4}$alkyl;

X is oxygen, NOR$^3$, N—NR$^4$R$^5$, or N—NHCONR$^4$R$^5$;

each of R$^1$, R$^2$, R$^3$, R$^4$, and R$^5$, independently from the others, is hydrogen, C$_{1-6}$alkyl, C$_{1-6}$acyl, benzoyl, C$_{1-4}$trialkylsilyl, benzyl, phenyl, or benzyl or phenyl substituted by C$_{1-6}$alkoxy, C$_{1-6}$alkyl, hydroxy, or halogen, or R$^4$ and R$^5$ together are C$_{2-6}$alkylene group, and the alkyl, alkylene, and acyl groups contained in the radicals are straight-chain or branched radicals; and each of Y and Z, independently from the other, is hydrogen, halogen, pseudo-halogen, OH, O—(C$_{1-6}$) alkyl, O—(C$_{1-6}$)acyl or O-benzoyl, or Y and Z together are oxygen or a carbon-carbon bond.

2. The compound according to claim 1 in which each of R, R$^1$, and R$^2$ is hydrogen, X is oxygen, and Y and Z together are oxygen.

3. A compound of the formula:

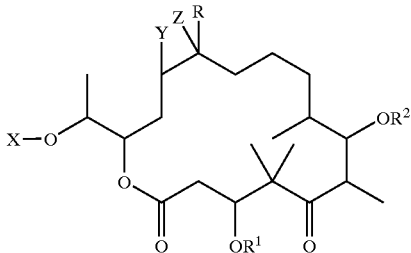

wherein

R is hydrogen or C$_{1-4}$alkyl;

X is hydrogen, C$_{1-8}$alkyl, C$_{1-8}$acyl, benzyl, benzoyl, or cinnamoyl;

each of R$^1$ and R$^2$, independently from the other, is hydrogen, C$_{1-6}$alkyl, C$_{1-6}$acyl, benzoyl, C$_{1-4}$trialkylsilyl, benzyl, phenyl, or benzyl or phenyl substituted by C$_{1-6}$alkoxy, C$_{1-6}$alkyl, hydroxy, or halogen, and the alkyl and acyl groups contained in the radicals are straight-chain or branched radicals; and each of Y and Z, independently from the other, is hydrogen, halogen, pseudo-halogen, OH, O—(C$_{1-6}$) alkyl, O—(C$_{1-6}$)acyl or O-benzoyl, or Y and Z together are oxygen or a carbon-carbon bond.

4. A pharmaceutical composition comprising a therapeutically effective amount of a compound according to either claim 1 or claim 3 in combination with a pharmaceutically acceptable carrier.

5. A pharmaceutical composition comprising a therapeutically effective amount of a compound of the formula:

(i)

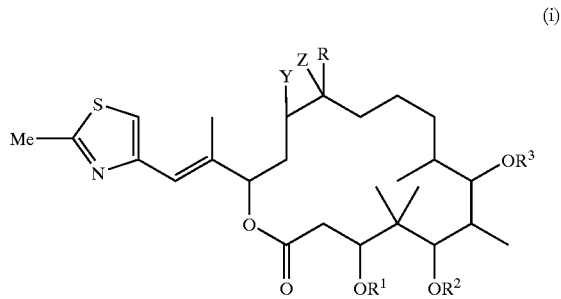

wherein

R is hydrogen or C$_{1-4}$alkyl;

each of R$^1$, R$^2$, and R$^3$, independently from the others, is hydrogen, C$_{1-6}$alkyl, C$_{1-6}$acyl, benzoyl, C$_{1-4}$trialkylsilyl, benzyl, phenyl, or benzyl or phenyl substituted by C$_{1-6}$alkoxy, C$_{1-6}$alkyl, hydroxy, or halogen, and the alkyl and acyl groups contained in the radicals are straight-chain or branched radicals; and each of Y and Z, independently from the other, is hydrogen, halogen, pseudo-halogen, OH, O—(C$_{1-6}$)

alkyl, O—(C$_{1-6}$)acyl or O-benzoyl, or Y and Z together are oxygen or a carbon-carbon bond;

(ii)

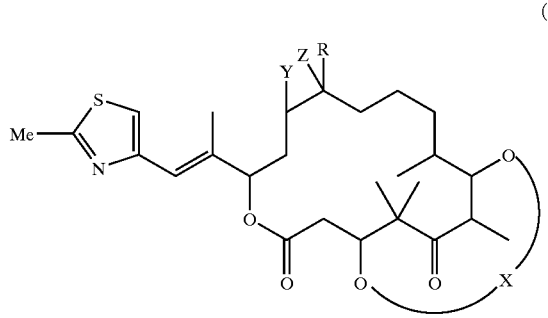

wherein

R is hydrogen or C$_{1-4}$alkyl;

X is —C(O)—, —C(S)—, —S(O)—, —CR$^1$R$^2$—, or —SiR$^2$— in which each of R$^1$ and R$^2$, independently from the other, is hydrogen, C$_{1-6}$alkyl, C$_{14}$acyl, benzoyl, C$_{1-4}$trialkylsilyl, benzyl, phenyl, or benzyl or phenyl substituted by C$_{1-6}$alkoxy, C$_{1-6}$alkyl, hydroxy, or halogen, or R$^1$ and R$^2$ taken together are C$_{2-6}$alkylene, and the alkyl, alkylene, and acyl groups contained in the radicals are straight-chain or branched radicals; and each of Y and Z, independently from the other, is hydrogen, halogen, pseudo-halogen, OH, O—(C$_{1-6}$) alkyl, O—(C$_{1-6}$)acyl or O-benzoyl, or Y and Z together are oxygen or a carbon-carbon bond;

(iii)

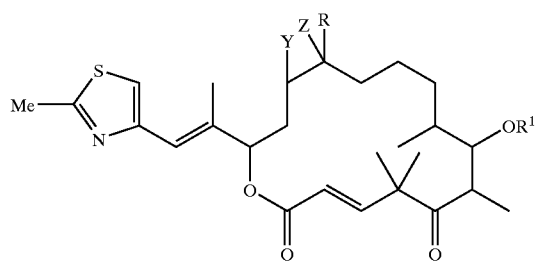

wherein

R is hydrogen or C$_{1-4}$alkyl;

R$^1$ is hydrogen, C$_{1-6}$alkyl, C$_{1-6}$acyl, benzoyl, C$_{1-4}$trialkylsilyl, benzyl, phenyl, or benzyl or phenyl substituted by C$_{1-6}$alkoxy, C$_{1-6}$alkyl, hydroxy, or halogen, and the alkyl and acyl groups contained in the radicals are straight-chain or branched radicals; and each of Y and Z, independently from the other, is hydrogen, halogen, pseudo-halogen, OH, O—(C$_{1-6}$) alkyl, O—(C$_{1-6}$)acyl or O-benzoyl, or Y and Z together are oxygen or a carbon-carbon bond; or (iv)

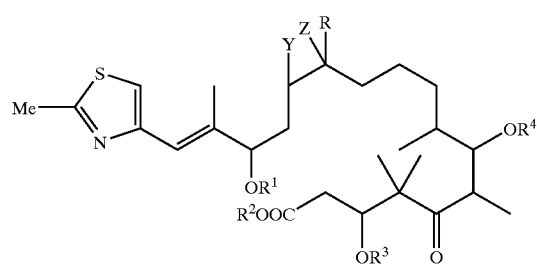

wherein

R is hydrogen or C$_{1-4}$alkyl;

each of R$^1$, R$^2$, R$^3$, and R$^4$, independently from the others, is hydrogen, C$_{1-6}$alkyl, C$_{1-6}$acyl, benzoyl, C$_{1-4}$trialkylsilyl, benzyl, phenyl, or benzyl or phenyl substituted by C$_{1-6}$alkoxy, C$_{1-6}$alkyl, hydroxy, or halogen, and the alkyl and acyl groups contained in the radicals are straight-chain or branched radicals, and each of Y and Z, independently from the other, is hydrogen, halogen, pseudo-halogen, OH, O—(C$_{1-6}$) alkyl, O—(C$_{1-6}$)acyl or O-benzoyl, or Y and Z together are oxygen or a carbon-carbon bond;

in combination with a pharmaceutically acceptable carrier.

6. The composition according to claim 4 in which in said compound, each of R, R$^1$, and R$^2$ is hydrogen, X is oxygen, and Y and Z together are oxygen.

* * * * *